United States Patent [19]

Hammock et al.

[11] Patent Number: 4,558,004

[45] Date of Patent: Dec. 10, 1985

[54] MONITORING PRENEOPLASTIC ANTIGEN

[75] Inventors: Bruce D. Hammock; Kenji Ota, both of Davis, Calif.

[73] Assignee: The Regents of the University of California, Berkeley, Calif.

[21] Appl. No.: 478,962

[22] Filed: Mar. 25, 1983

[51] Int. Cl.$^4$ .......... C12Q 1/00; C12Q 1/34; G01N 33/54
[52] U.S. Cl. .......... 435/4; 435/7; 435/18
[58] Field of Search .......... 435/4, 7, 18, 188, 810; 436/813

[56] References Cited

PUBLICATIONS

Kuhlmann et al., Biochem. Biophys. Res. Comm., 98(2): 417–423, (1981).
Levin et al., PNAS USA, 75(7): 3240–3243 (1978).
Thomas et al., Chemical Abstracts, 97: 87503r, p. 331 (1982).
Watabe et al., Biochem. Biophys. Res. Comm., 44(1): 199–204 (1971).
Gill et al., Chemical Abstracts, 98: 30195h, (1982).
Novikoff et al., PNAS USA, 76(10): 5207–5211 (1979).

Primary Examiner—Esther M. Kepplinger
Attorney, Agent, or Firm—Townsend & Townsend

[57] ABSTRACT

Methods and compositions are provided for the detection of preneoplastic antigen (microsomal epoxide hydrolase) in serum. The presence of PNA is associated with abnormal liver conditions, including neoplastic and preneoplastic lesions and hepatocellular carcinoma.

10 Claims, No Drawings

MONITORING PRENEOPLASTIC ANTIGEN

BACKGROUND OF THE INVENTION

1. Field of the Invention

Hepatocellular carcinoma (liver cancer) is a very common form of cancer. Detection of hepatocellular carcinoma is problematic, often resulting in late diagnosis. Late diagnosis, in turn, can render treatment ineffective due to the advanced state of the disease and the extent of liver involvement.

A blood test capable of sensitive and accurate detection of hepatocellular carcinoma would be most useful. Such a test could be used to screen patients for early detection of the cancer at a stage where it could still be treated. The test could also be used with patients undergoing treatment to continuously monitor the status of the disease.

At present, the best serological test for hepatocellular carcinoma is the measurement of α-fetoprotein. While this test is widely used and has proved to be a highly useful tool in cancer detection, it suffers from certain drawbacks. Elevated serum α-fetoprotein levels do not occur much earlier than other clinical symptoms, and not all liver tumors result in such increases in α-fetoprotein. Moreover, elevated α-fetoprotein titers are present in normal individuals, most notably being associated with infancy, pregnancy and periods of liver regeneration. Thus, an α-fetroprotein assay is at best equivocal and is entirely unsuitable for patients who are pregnant, who are infants, or who have undergone liver surgery. The latter class includes individuals who have undergone surgery for the removal of liver tumors where it would be of great benefit to monitor for possible recurrence.

Thus, it is desirable to provide for the detection in serum of an alternate tumor antigen or tumor marker which can be related to the presence of liver cancer. In particular, it would be desirable to provide a serum assay capable of detecting preneoplastic conditions in the liver.

2. Description of the Prior Art

Farber and his co-workers identified a soluble protein associated with hepatic preneoplastic lesions in rats. This protein was called preneoplastic antigen (PNA). See, Farber (1973) Methods in Cancer Research VII, page 345; Okita et al. (1974) Cancer Research 34:2758; Okita and Farber (1975) Gann Monograph on Cancer Research 17:283-299; and Okita et al. (1975) J. Natl. Cancer Inst. 54:199-202. PNA was shown to be microsomal epoxide hydrolase by Levin et al. (1978) Proc. Natl. Acad. Sci. USA 75:3240-3243. Levin et al. failed to detect microsomal epoxide hydrolase activity in the serum of rats suffering from hepatocellular carcinoma. Microsomal epoxide hydrolase activity in the cytosol of rat liver cells has been shown to be induced following exposure to certain carcinogens and to be at very high levels in hepatic neoplastic nodules. Novikoff et al. (1979) Proc. Natl. Acad. Sci. USA 76:5207. An enzyme-linked immunosorbent assay for the detection of microsomal epoxide hydrolase was used to detect the hydrolase in rat microsomal proteins and rat liver cytosol. Gill et al. (1982) Carcinogenesis 3:1307-1310.

SUMMARY OF THE INVENTION

Methods and compositions are provided for the early detection of hepatic neoplasms and preneoplasms. The method comprises withdrawing a serum sample from a human or other vertebrate and assaying the serum sample for the presence of microsomal epoxide hydrolase or preneoplastic antigen (PNA). The presence of PNA in serum has been found to be characteristic of liver abnormality, in particular the occurrence of preneoplastic and neoplastic lesions and nodules and hepatocellular carcinomas. Patients displaying detectable levels of serum PNA should be further diagnosed to determine the cause. The method is particularly useful in combination with other screening assays, such as an assay for α-fetoprotein, to provide a comprehensive test for liver cancer.

DESCRIPTION OF THE SPECIFIC EMBODIMENTS

A serum assay is provided for the detection of preneoplastic antigen (PNA), which assay is useful for the early detection of neoplastic and preneoplastic conditions in the liver. PNA is a protein (microsomal epoxide hydrolase) and can be detected by any one of a wide variety of techniques suitable for the detection of protein. The technique should be capable of detecting PNA at levels of about 1 ng/ml, preferably about 0.1 ng/ml, more preferably 0.001 ng/ml and below.

Suitable assay techniques include both immunological and enzymatic methods. The immunological detection methods rely on the production of antibodies, which may be obtained by injecting the PNA into a wide variety of vertebrates in accordance with conventional techniques. Usually, the animals are bled periodically with successive bleeds having improved titer and specificity. The antigens may be injected intramuscularly, intraperitoneally, subcutaneously, or the like. Usually a vehicle is employed, such as complete or incomplete Freund's adjuvant. If desired, monoclonal antibodies can be prepared according to the now classic teachings of Kohler and Milstein (1976) Eur. J. Immunol. 6:511-519.

Once antibodies having suitable specificity have been prepared, a wide variety of immunological assay methods are available. Numerous competitive and non-competitive protein binding assays have been described in the scientific and patent literature, and a large number of such assays are commercially available. Exemplary immunoassays which are suitable for detecting the PNA in serum include those described in U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. In many cases, it will be necessary to pretreat the serum sample in some manner prior to performing the immunoassay.

Particularly preferred are sensitive enzyme linked immunosorbent assay (ELISA) methods which are described in detail In U.S. Pat. Nos. 3,791,932; 3,839,153; 3,850,752; 3,879,262; and 4,034,074. Such ELISA assays can provide measurement of the PNA at concentrations as low as 1 ng/ml and below.

According to the preferred ELISA technique, the PNA is bound either covalently or non-covalently to a solid surface. After washing the surface to remove weakly-bound and unbound proteins, the serum sample is mixed in an appropriate buffer, combined with enzyme-labeled antibodies, and incubated for sufficient time to allow binding of the PNA to the labeled antibodies. To the extent that the serum sample contains PNA, the labeled antibody is bound to the free PNA and unavailable for binding to the immobilized PNA on the solid surface. After washing the solid surface to remove all non-specifically bound proteins, substrate for the labeling enzyme is added in an appropriate buffer to produce a detectable signal, normally light absorption, which can be related to the amount of enzyme label remaining on the surface. By employing a standard curve, which is generated using known amounts of PNA, the observed absorption may be correlated with the concentration of PNA in the serum sample.

The presence of PNA in serum can be detected at even lower concentrations by directly observing the enzyme activity. Epoxide hydrolases hydrate cyclic ethers to 1,2-diols. While both microsomal nuclear and mitochondrial cytosolic epoxide hydrolases exist, they can be distinguished based on substrate selectivity, as well as other factors. In particular, microsomal epoxide hydrolase will selectively hydrate cis-stilbene oxide at high pH. By observing the subsequent formation of cis-stilbene diol, the enzyme activity can be determined. A particular protocol is described in the Experimental section hereinafter.

It is probable that both active and inactive (denatured) PNA are present in serum. As demonstrated in the Experimental section, PNA activity of about 1 pmole/hr-ml and below is observed in normal serum. This activity increases to about 3 to 5 pmole/hr-ml and above in patients suffering from liver abnormality. Moreover, it is likely that the levels of inactive PNA will be higher in both normal patients and those suffering from liver preneoplasms and neoplasms. Thus, the observed PNA level which is considered indicative of liver cancer and other abnormalities will depend on the assay method employed. The enzymatic assay, which measures only the active enzyme, will be considered positive for observed activities above about 1 pmole/hr-ml, the upper limit of the normal range. This activity is equivalent to a serum PNA concentration of about $2 \times 10^{-2}$ ng/ml. An immunoassay, which can measure inactive as well as active PNA, will be positive at serum PNA concentrations which are somewhat higher, probably in the range from about 0.1 to 1 ng/ml, or higher.

The following experimental results are offered by way of example and not by way of limitation.

EXPERIMENTAL

The following abbreviations are employed: CSO—cis-stilbene oxide; dpm—decays per minute; PMSF—phenylmethylsulfonyl fluoride; tlc—thin layer chromatography.

Enzymatic assays for PNA in human serum were performed as follows. Unhemolyzed serum was diluted 1:1 with 100 mM tris-HCl (pH 9.0, 30° C.) which contained 0.5 mM PMSF. $^3$H-CSO (250,000 dpm, 15 Ci/mmole) in ethanol (1 μl) was added to 50 μl of the diluted serum. The final substrate concentration was $1.5 \times 10^{-7}$ M. Tubes were then covered with parafilm to minimize evaporation and incubated at 37° C. for three hours. Methanol (25 μl) containing cold CSO and diol standards were then added to the tubes. The tubes were vortexed and centrifuged using a table-top centrifuge. Two aliquots (25 μl) of each of the supernatants were streaked onto the cellulose prelayer of Whatman LK 5DF Hc plates which were dried at room temperature. The plates were developed in methanol up the cellulose-silica gel boundary, and removed and dried. The plates were then developed in toluene:n-propanol (20:1). Spots corresponding to the diol standard were scraped into vials containing ACS scintillation cocktail. The vials were then counted after sitting in the dark for 24 hours to reduce chemiluminescence.

Serum samples from 117 apparently normal donors were assayed for PNA as just described. The mean observed PNA activity was $0.3 \pm 0.4$ pmoles/hr-ml. Twenty serum samples from patients at a cancer clinic were also assayed for PNA activity. Of these patients, only one suffered from hepatocellular carcinoma. The PNA level in this patient was above 5 pmoles/hr-ml. The remaining patients displayed a mean serum PNA activity of $0.4 \pm 0.2$ pmole/hr-ml. Serum samples from 29 patients suffering from Kaposi's sarcoma were tested. Several patients showed elevated serum PNA levels and it is suspected that metastases to the liver had occurred. The mean serum PNA level for all of these patients was $1.1 \pm 0.9$ pmoles/hr-ml.

In accordance with the subject invention, a sensitive assay is provided for detecting the presence of PNA in serum. The presence of PNA, in turn, is characteristic of neoplastic and preneoplastic lesions in the liver, including hepatocellular carcinoma. Thus, the serum assay for PNA promises to have wide spread application in cancer diagnostics, and in particular in the diagnosis of hepatic tumors.

Although the foregoing invention has been described in some detail by way of illustration and example for purposes of clarity and understanding, it will be obvious that certain changes and modifications may be practiced within the scope of the appended claims.

What is claimed is:

1. A method for identifying hepatic preneoplastic or neoplastic lesions in a vertebrate, said method comprising:
   taking a serum sample from the vertebrate;
   assaying said sample to determine the amount of microsomal epoxide hydrolase present therein; and
   comparing the determined amount of microsomal epoxide hydrolase with a predetermined level which level is diagnostic of hepatic preneoplastic or neoplastic lesions.

2. A method as in claim 1, wherein the step of assaying comprises an immunoassay.

3. A method as in claim 1, wherein the step of assaying comprises introducing into the serum sample a substrate for microsomal epoxide hydrolase and observing the formation of product.

4. A method as in claim 3, wherein the substrate is cis-stilbene oxide and the product is stilbene diol.

5. A method as in claim 1, wherein the vertebrate is a human.

6. A method for detecting hepatocellular carcinoma in a patient, said method comprising:
   taking a serum sample from said patient;
   assaying said serum sample for the presence of microsomal epoxide hydrolase; and
   further examining the patient if the level of microsomal epoxide hydrolase is above a predetermined level.

7. A method as in claim 6, wherein said step of assaying comprises an immunoassay.

8. A method as in claim 6, wherein said step of assaying comprises introducing into the serum sample a substrate for microsomal epoxide hydrolase and observing the formation of product.

9. A method as in claim 8, wherein the substrate is cis-stilbene oxide and the product is stilbene diol.

10. A method as in claim 6, wherein the predetermined level of microsomal epoxide hydrolase corresponds to an activity of about 1 pmole/hr-ml.

* * * * *